United States Patent [19]

Brundidge et al.

[11] Patent Number: 4,625,020

[45] Date of Patent: Nov. 25, 1986

[54] NUCLEOSIDE PROCESS

[75] Inventors: Steven P. Brundidge, Wolcott; Henry G. Howell; Chester Sapino, Jr., both of East Syracuse, all of N.Y.; Chon-Hong Tann, Berkeley Heights, N.J.

[73] Assignee: Bristol-Myers Company, New York, N.Y.

[21] Appl. No.: 574,329

[22] Filed: Nov. 18, 1983

[51] Int. Cl.$^4$ .................... C07H 15/00; C07H 15/06
[52] U.S. Cl. .................................. 536/18.2; 536/118; 536/119
[58] Field of Search .................... 536/23, 24, 26, 18.4, 536/54, 122, 118

[56] References Cited

U.S. PATENT DOCUMENTS 4,211,773  7/1980  Lopez et al. ..................... 424/180

OTHER PUBLICATIONS

Ness and Fletcher, J. Amer. Chem. Soc. 78, 4710–14 (1956).
Ibid., 76, 1663–6 (1954).
Reichman et al., A Practical Synthesis of 2-Deoxy-2--Fluoro-D-Arabinofuranose Derivatives, Carbohydrate Research 42, 233 (1975).
Ritzmann, Nucleosides LXXXIX, Synthesis of 1-(2--Chloro-2-Deoxy-(α and β)-D-Arabinofuranosyl)-Cytosines, Carbohydrate Research 39, 227 (1975).
Stevens et al., The Proton Magnetic Resonance of Pentofuranose Derivatives, J. Org. Chem. 33(5), 1799–1805 (1968).
Chavis et al., Synthesis of 1,3,5-Tri--O-Acyl-α-±-D-Ribofuranoses Substituted at Position 2, Chem. Abstracts 89: 180298x (1978).

*Primary Examiner*—Ethel G. Love
*Attorney, Agent, or Firm*—Robert E. Carnahan

[57] ABSTRACT

Process for producing 1-halo-2-deoxy-2-fluoroarabinofuranoside derivatives bearing protective ester groups from 1,3,5-tri-O-acylribofuranose; the 1-halo compounds are intermediates in the synthesis of therapeutically active nucleosidic compounds.

7 Claims, No Drawings

NUCLEOSIDE PROCESS

DESCRIPTION OF THE PRIOR ART

2-Deoxy-2-fluoroarabinofuranosyl halides of the formula

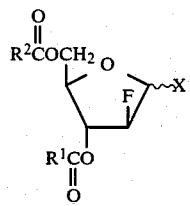

VII wherein $R^1$ and $R^2$ are carbonyl attached organic groups such as the aliphatic or aromatic hydrocarbon residues of carboxylic acyl groups and X is fluorine, chlorine, bromine, or iodine are required as intermediates for the production of synthetic nucleosidic compounds having chemotherapeutic activity including those of the Formula IX wherein inter alia A may be OH or $NH_2$, B is an oxygen atom, and Y is a halogen atom including Cl, Br, I, and F or a methyl group. Z is methylene (—CH=) or nitrogen.

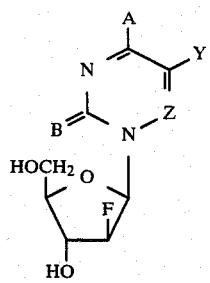

IX

The nucleosidic compounds including those of Formula IX are the subject of U.S. Pat. No. 4,211,773 patented July 8, 1970 which discloses their preparation from VII. The entire disclosure of U.S. Pat. No. 4,211,773 is incorporated herein by reference.

The present invention provides a process for production of the compounds of Formula VII, intermediates useful in that process, and in transforming VII into the chemotherapeutic end products of Formula IX.

The compounds of Formula VII have heretofore been produced by a five-step eight-reaction sequence from 1,2:5,6-di-O-isopropylidene-3-O-tosyl-α-D-allofuranose which was in turn obtained from glucose by a further sequence of four reactions. The production of the compounds of Formula VII by this method is described in the literature by Reichman et al. Carbohydrate Research, 42 (1975) 223–240, and Ritzmann et al. ibid, 39 (1975) 227–236. This prior method while amenable to large scale synthesis, is long and cumbersome and disadvantageous for a commercial process.

SUMMARY OF THE INVENTION

The improved process of the present invention for the production of the compounds of Formula VII is illustrated in the following Process Scheme by the transformations of Steps 4, 5, and 6.

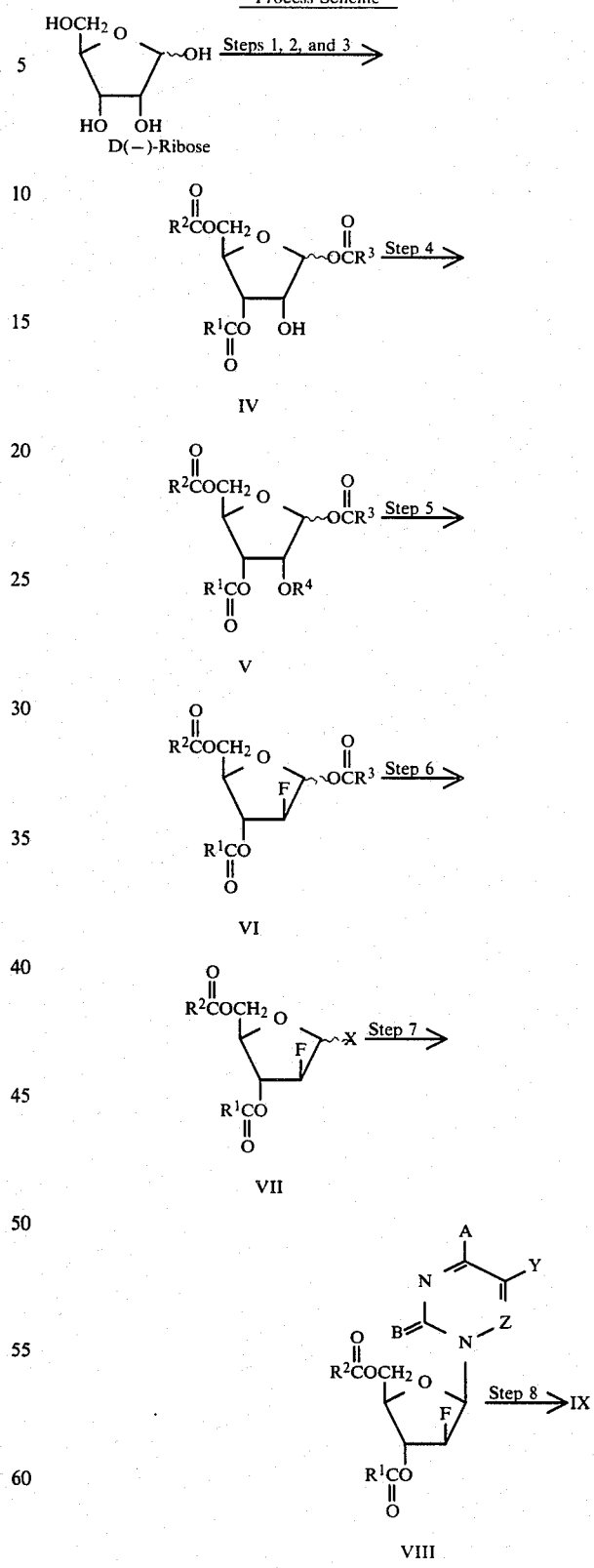

In the foregoing scheme $R^1$, $R^2$, and $R^3$ are the organic residues of carboxylic acyl groups apart from the carbonyl portion thereof wherein said acyl groups are selected from alkanoyl having 1 to 20 carbon atoms such as formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, arachidonyl and the like. $R^1$, $R^2$, and $R^3$ can also be aroyl such as benzoyl and naphthoyl wherein the aromatic group may be additionally substituted by alkyl, alkoxy, halo, or nitro moieties such as p-toluoyl, p-anisoyl, p-chlorobenzoyl, p-nitrobenzoyl or 2,4-dinitrobenzoyl and the like. $R^2$ may also be adamantoyl. X is fluorine, chlorine, bromine, or iodine.

DETAILED DESCRIPTION OF THE INVENTION

Compound IV represented by 1,3,5-tri-O-benzoyl-α-D-ribofuranoside and the first three steps of the process involving its production are known. Refer to Ness and Fletcher, J. Amer. Chem. Soc. 78, 4710–14 (1956), ibid., 76, 1663–7 (1954), and the earlier article referred to therein Ness, Diehl, and Fletcher, ibid, 76, 763–7 (1954).

Step 4 is an esterification of the 2-hydroxyl group of the ribose derivative IV to produce the imidazosulfonyl, or fluorosulfonyl ester V. The $R^4$ substituent in Formula V refers to the 1-imidazosulfonyl, or to the fluorosulfonyl group ($-SO_2F$). The selection of this ester is unique for the present process since it is facilely displaced by fluoride (Step 5) with inversion of the configuration at this carbon atom to yield the 2-deoxy-2-fluoroarabinofuranoside derivative VI. The displacement is effected with potassium acid fluoride ($KHF_2$).

The imidazosulfonyl ester of Formula V is produced by methods which are established in the art for the preparation of imidazosulfonyl esters. The imidazosulfonyl group is a well-known protecting/leaving group which has been rather widely applied in synthetic organic chemistry. It is preferred to carry out the reaction by treatment of the tri-O-benzoyl ribofuranoside first with sulfuryl chloride at reduced temperature followed by treatment of the mixture with imidazole. A bright yellow solution is produced when methylene chloride is used for the reaction solvent in accordance with a preferred embodiment. The reaction comes to completion within about 2 hrs. at room temperature. The product is recovered from the methylene chloride solution by evaporation of the solvent and recrystallization of the crude material from acetone/water. It can also be recovered from the methylene chloride reaction mixture by treatment thereof with a non-solvent for the product such as hexane.

Step 5 is a displacement of the imidazosulfonyl or fluorosulfonyl ester group by fluoride. It has been found that potassium acid fluoride ($KHF_2$) is the preferred source of fluoride for the displacement. Other fluoride compounds that are frequently used in displacement reactions of this sort such as tetrabutylammonium fluoride or KF are unsuited as fluoride sources. In the case of tetrabutylammonium fluoride side reactions of the reagent with the tri-O-benzoyl arabinose ester predominate to the substantial exclusion of the desired displacement reaction. Moreover, application of the process to other 1,3,5-tri-O-benzoyl-α-D-ribofuranoside-2-esters such as the 2-O-trifluoromethylsulfonyl and the 2-O-methanesulfonyl esters does not result in efficient displacement of the 2-O-ester group with fluoride to the exclusion of undesired side reactions as is the case with the 1-imidazosulfonyl ester. At least about 2 moles of $KHF_2$ and preferably 4 to 8 moles of $KHF_2$ per mole of Formula V reactant are employed.

The displacement reaction using potassium acid fluoride with the imidazosulfonyl or fluorosulfonyl ester of Formula V can be carried out under a variety of conditions, but we prefer to carry it out in the presence of strong aqueous acid. Any strong acid including the organic carboxylic, sulfonic, or phosphonic acids or the mineral acids can be used which is otherwise non-reactive under the prevailing reaction conditions with the other functional groups in the reactant of Formula V. Some suitable acids are acetic, phosphoric, sulfuric, methanesulfonic, toluenesulfonic, trifluoroacetic, hydrofluoric, hydrochloric, formic. Most preferred is aqueous hydrofluoric acid. From about 0.5 to 2 moles and preferably 0.9 mole of HF per mole of $KHF_2$, employing ethylene glycol, butanediol or other liquid aliphatic polyol having from 2 to 6 carbon atoms as reaction medium. The reaction medium is chosen from the stable (under the prevailing reaction conditions) liquid organic compounds such as the alkanols, alkanpolyols, cyanoalkanes, alkanoamides, ethers, alkoxyalkanols, and polyethers having molecular weights in the range of about 30 to 200. It is preferred to employ those liquid media having boiling points equal to a higher than the selected reaction temperature. Preferred media are acetonitrile, butanol, tert.-butanol, formamide, ethylene glycol, and 2,3-butanediol. The most preferred media respond to the Formula $R^aOAlkOR^b$ wherein $R^a$, and $R^b$ are selected from the group consisting of H, alkyl, or alkoxyalkyl each having up to 6 carbon atoms, and Alk is an alkylene group containing from up to 6 carbon atoms. Alk may be straight or branced. $R^aO$ and $R^bO$ may be attached to adjacent or more distant carbon atoms.

The reaction is carried out at elevated temperature, but the precise temperature employed is not critical so long as it is within the range of about 75° C. to 170° C. We prefer to carry out the process at about 130° to 145° C. At lower temperatures within the range of about 60°–120° C. an intermediate reaction product of the reaction between the imidazosulfonyl ester of Formula V and $KHF_2$ is produced. Based upon NMR spectral evidence, it is believed to be the fluorosulfonyl ester of Formula V; in one specific example that substance of Formula V wherein $R^1$, $R^2$ and $R^3$ are phenyl and $R^4$ is $-SO_2F$ was obtained. This intermediate reacts upon further heating in the presence of $KHF_2$ to form the desired 2-deoxy-2-fluoroarabinose derivative of formula VI as pictured in the Process Scheme. The formation of the intermediate and transformation thereof to the Formula VI product can be readily followed by HPLC.

Minimal amounts of solvent medium are required, from 1 to 5 ml. per gram of starting imidazosulfonyl ester, and the product is recovered by quenching the reaction mixture with ice water and extracting the product from the aqueous mixture with a water immiscible solvent, preferably methylene chloride. The desired fluoro compound can be recovered from the extract by conventional means involving evaporation of the solvent and chromatography of the residue, but it is not necessary to purify this intermediate. The methylene chloride reaction solution after concentration to a manageable volume may be used directly in the next reaction step.

Production of the 2-deoxy-2-fluoroarabinose derivative by the fluoride displacement reaction of the present process represents a substantial advance over the prior art. The fluoride displacement step of the Reichman et al. (loc. cit.) process requires molten acetamide as reaction medium and temperatures of about 200° C. Acetamide in large amounts at high temperature is expensive and hazardous for a large scale operation.

Conversion of the 2-fluoro-1,3,5-triester of Formula VI to the 1-bromo, 1-chloro, 1-iodo, or 1-fluoro compound of Formula VII in Step 6 may be carried out in a known fashion by treatment with hydrogen bromide, hydrogen chloride, or hydrogen fluoride under non-hydrolytic conditions such as in an anhydrous solvent. The iodo compounds are made from the chloro, or bromo compounds by an exchange reaction, e.g. KI in acetone. The method used by Reichman (loc. cit.) for the preparation of 3-O-acetyl-5-O-benzoyl-2-deoxy-2-fluoro-D-arabinofuranosyl bromide from the corresponding 1-O-acetyl compound is satisfactory. This involves treatment of the 1,3,5-triester dissolved in methylene chloride with HBr in acetic acid. Other halogenated alkanes having 1 to 4 carbon atoms and 2 to 10 chlorine or bromine atoms may be used as solvent.

The 1-bromo, 1-chloro, 1-fluoro, or 1-iodo compound of Formula VII may then be used in reaction with the pyrimidine compound of the formula

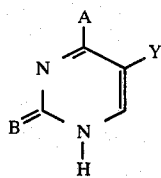

in known fashion to produce the nucleosidic compound of Formula VIII. The pyrimidine compound is fully silylated prior to carrying out the reaction in accordance with the instructions in U.S. Pat. No. 4,211,773 (loc. cit.). By "fully silylated" is meant that all active hydrogen atoms of any hydroxy or amino groups present which may serve as the competing reaction sites for the furanosyl halide of Formula VII are blocked by silyl groups such as the trimethylsilyl group. Alternatively, the compound of Formula VI may react directly with the foregoing silylated pyrimidine compound to product Formula VIII which, in effect, omits Step 6. The product of Formula IX is then produced by hydrolysis of the reaction product VIII to remove remaining silyl and $R^1CO$, and $R^2CO$ groups.

The intermediates of Formulas V, VI, and VII wherein each of $R^1$, $R^2$, and $R^3$ is an aromatic group as defined herein are preferred since the yields provided in their production by the present process are higher. Those of Formula VIIa are believed to afford enriched proportions of the $\beta$-arabinofuranosylnucleosides of Formula VIIIa relative to the $\alpha$-isomers when used in the conventional preparative methods. The art presently prefers the $\beta$-isomer of the nucleosides of Formula IX for biological purposes. Those compounds of Formula V, VI, VII, and VIII wherein $R^1$, $R^2$, and $R^3$ are aromatic groups are referred to herein as Formulas Va, VIa, VIIa, and VIIIa and are considered part of the present invention.

EXAMPLES

Procedure 1 (Steps 1, and 2)
1-O-Methyl-2,3,5-tri-O-benzoyl-$\alpha$-D-ribofuranoside.

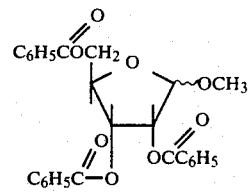

The procedure of Ness, Diehl, and Fletcher, (loc. cit.) appearing at page 765 as follows is adapted for the present process.

"Five grams of pure, powdered D-ribose ($[\alpha]^{20}D-20°$, equilibrium in $H_2O$) was added to 120 ml. of methanol containing 1% of hydrogen chloride (0.216N) and the mixture stirred until solution was complete. After approximately 45 minutes at room temperature (27°) test of sample of the mixture with Fehling solution showed that the reducing power had almost disappeared and 6 ml. of pyridine was then added. The reaction mixture was concentrated in vacuo at 30°–35° to a stiff sirup which was dissolved in 50 ml. of pyridine and the resulting solution, after cooling, treated with 14 ml. of benzoyl chloride. After the reaction was largely complete, the mixture was held at 40° for 1.5 hr., cooled and treated with a chip of ice to decompose the excess of benzoyl chloride. The reaction mixture was then diluted with methylene dichloride and washed successively with cold water, cold 3N sulfuric acid and aqueous sodium bicarbonate, moisture finally being removed with sodium sulfate. The solution was filtered through carbon and concentrated in vacuo (35°–40° bath) to a heavy sirup".

Procedure 2 (Step 3)
1,3,5-Tri-O-benzoyl-D-ribofuranoside (Formula IV).

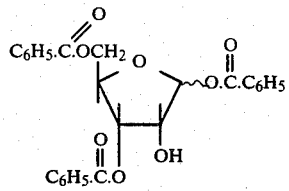

The crude 1-O-methyl-2,3,5-tri-O-benzoyl-ribofuranoside which had been made from 100 g of D(−)-ribose (0.67 mole) as in Procedure 1 is dissolved in 640 mL of dry $CH_2Cl_2$. The solution is stirred at 22° C., protected from moisture with a $CaCl_2$ drying tube and 500 mL of 30% (wt/vol) HBr in acetic acid (Fisher), (1.85 mole, 2.76 equivalents, HBr) is added over a 15 min. period. Aliquots (1 mL) are removed at 30 min. intervals and analyzed for the absence of the starting material by high performance liquid chromatography (HPLC). HPLC done on $C^{18}$, reverse phase column column using 35% $H_2O$, 65% $CH_3CN$. Starting material residence time (Rt) at flow rate of 1.5 mL/min. is 6.7 min. After 1½ hrs. no starting material is detectable. The solution is poured into a separatory funnel and washed with four portions of ice water, twice with saturated NaHCO₃ solution and once with brine. The CH₂Cl₂ is removed under reduced pressure at 30° C. to yield the crude furanosyl bromide as a dark syrup. [360 MHz NMR (CD₂Cl₂): α-isomer; 6.98, d, 1H; 5.45, dd, 1H; 4.94, dd, 1H; 4.64–4.9, m, 2H; 7.3–8.2, m, 15H: β-isomer; 6.57, s, 1H; 6.08, d, 1H, 6.24, dd, 1H; 5.02, m, 1H; 4.65–4.9, m, 2H; 7.3–8.2, m, 15H]. The crude furanosyl bromide is dissolved in 1200 mL of acetone and 60 mL H₂O. After 1½ hrs. the reaction solution is poured into a separatory funnel with 1 L CH₂Cl₂ and washed once with cold H₂O, twice with saturated NaHCO₃ and once with brine. The organic solution is concentrated to about 750 mL and diluted slowly with portions of hexane (1500 mL) until crystals began to form. Crystallization is complete after 18 hrs. at 20° C. and the solids are removed by filtration. A second crop may be obtained from the filtrate by evaporating to a syrup, redissolving in 250 mL CH₂Cl₂ and diluting to the cloud point with hexane (1400 mL). After cooling in an ice bath for 1½ hrs., the second crop is collected by vacuum filtration and washed with 3 portions of cold ¼; CH₂Cl₂/hexane. The combined weight of the two crops of white solid is 121 g (39% of theory), mp, 140°–141° C. [360 MHz NMR (CD₂Cl₂): 6.64, d, 1H; 4.75, m, 1H, 5.59, dd, 1H; 4.76–4.5, m, 3H; 2.60, d, 1H, 7.3–8.2, m, 15H. Elemental analysis calculated: %C 67.52, %H 4.80. Found: %C 67.39, %H 4.82. IR (KBr) aromatic 3020, 1605, 710 cm⁻¹, CH₃, CH₂, CH 2940 cm⁻¹, ester 1720, 1270 cm⁻¹, C-O, 1110 cm⁻¹.]

Procedure 3 (Step 4)
2-Imidazosulfonyl-1,3,5-tri-O-benzoyl-α-D-ribofuranoside (Formula V.

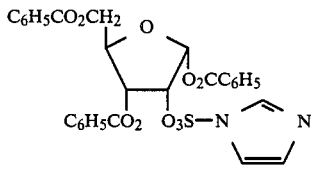

A slurry containing 85 g (0.184 mole) of 1,3,5-tri-O-benzoyl-α-D-ribofuranoside in 700 mL dry CH₂Cl₂ is stirred protected from moisture with a CaCl₂ drying tube. The mixture is cooled on a salt-ice bath to −20° C. and 49.7 g (30 mL, 0.368 mole) sulfuryl chloride is added slowly from a dropping funnel. Addition should be completed in about 20 min. and 200 mL dry CH₂Cl₂ is then added through the dropping funnel to wash down the solids. Imidazole is added in 5 equal portions totaling 125 g (1.84 mole, 10 equivalents). The cooling bath is removed and the reaction continued for 2 hrs. The bright yellow reaction mixture cntaining a small amount of white solid is transferred to a separatory funnel. The organic layer is washed four times with 400 mL water containing 10 drops of 1N HCl and twice with water. After drying over Na₂SO₄, the CH₂Cl₂ solution (~1200 mL) is diluted to the cloud point with 2 L of hexane and seeded. Crystallization is completed by keeping the mixture at 0° to 5° overnight (16 hrs.) and the product is collected by filtration. A second crop is collected after adding 700 mL of hexane to the filtrate. The yield of product is 93.9 g. A portion of the material (79 g) is dissolved in 1500 mL boiling acetone, filtered hot and diluted with 350 mL of boiling water. A cloudy solution results and is seeded and allowed to crystallize at 22° C. for 16 hrs. The mixture is cooled in an ice bath 2 hrs. and the crystals removed by filtration.

The yield of recrystallized product is 69 g (mp. 129–130.5. [360 MHz NMR (CD₂Cl₂): 6.67, d, 1H; 5.28, dd, 1H; 5.63, dd, 1H; 4.81, dd, 1H; 4.65, octet, 2H; 6.9–8.2, m, 18H. Elemental analysis calculated: %C 58.78, %H 4.08, %N 4.73. Found: %C 58.59, %H 4.09, %N 4.73. IR (KBr) aromatic 3130, 1600, 705 cm⁻¹; ester 1720, 1225 cm⁻¹; O-SO₂ 1425, 1200 cm⁻¹.]

Procedure 4 (Step 5)
2-Deoxy-2-fluoro-1,3,5-tri-O-benzoyl-α-D-arabinofuranoside (Formula VI).

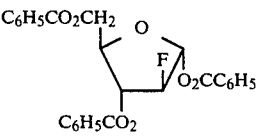

A slurry of 2-imidazosulfonyl-1,3,5-tri-O-benzoyl-α-D-ribofuranoside (13.0 g, 0.0219 mole), 26 mL of 2,3-butanediol, 6.86 g (0.0878 moles) KHF₂ and 2 mLs 50% HF (in H₂O, d=1.56, 0.078 mole) is prepared. The dark mixture is heated to 135° C. in an oil bath in a reaction flask equipped with an air condenser. The reaction progress is monitored by HPLC (70 Acetonitrile/30 H₂O, UV at 282 nm, 2.0 mLs/min., Whatman C-18 Reverse Phase Column) by taking a small aliquot (100 μL) and quenching with MeOH/H₂O and injecting a suitable volume on the HPLC. The desired product is eluted at 7.78 min. The reaction is allowed to proceed for 2.5 to 3.0 hrs. when product formation is maximal. The hot (135° C.) reaction mixture is thereupon quenched into 200 mL of a mixture of ice and water (100 mLs) with methylene chloride (100 mLs) with vigorous agitation. The liquid layers are separated and the aqueous layer is extracted with additional CH₂Cl₂ (100 mLs). The combined CH₂Cl₂ extracts are washed with dilute NaHCO₃ (75 mLs, 10% w/v, H₂O (75 mLs), and dried over anhydrous Na₂SO₄. The dry CH₂Cl₂ is treated with 20 g of decolorizing carbon, (25° C., 1 hr.) filtered through a filter aid and concentrated at reduced pressure to approximately 25 mL. HPLC analysis on Whatman C-18 Reverse Phase Column; 70% CH₃CN:30% H₂O; UV detection at 282 nm; flow rate 2.0 mLs/min. Four major components; the starting material (Rt 5.0 min.), the intermediate fluorosulfonyl ester (Rt 7.8 min.), the product (Rt 7.0 min.), and polar products resulting from debenzoylation (Rt 0 to 2 min.) indicates 65% 2-deoxy-2-fluoro-1,3,5-tri-O-benzoyl-α-D-arabinofuranoside. This product is used directly in the next step.

Procedure 5 (Step 6)
2-Deoxy-2-fluoro-3,5-di-O-benzoylarabinofuranosyl Bromide (Formula VII)

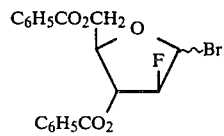

A solution of 2-deoxy-2-fluoro-1,3,5-tri-O-benzoyl-α-D-arabinofuranoside (0.0142 mole) and 25 mL dry CH₂Cl₂ is stirred magnetically with 8.3 mL 30% HBr/HOAc (2.49 g HBr 0.031 mole) at 25° C. for 16 hrs. The dark solution is washed twice with 75 mLs ice H₂O and once with cold 10% NaHCO₃ dried (Na₂SO₄),

Procedure 6 (Step 7)
1-(3,5-Di-O-benzoyl-2-deoxy-2-fluoro-α-D-arabinofuranosyl)-5-iodouracil (Formula VIII).

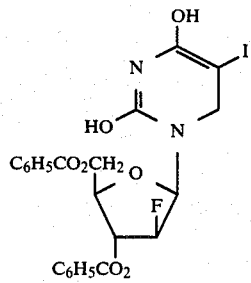

2,4-Di-O-trimethylsilyl-5-iodouracil is prepared by treating 4.03 g (0.0169 mole) 5-iodouracil in 60 mL dry CH₃CN containing 0.20 g (0.0015 mole) (NH₄)₂SO₄ at 40° C. with hexamethyldisilazane (3.03 g, 3.94 mL, 0.0188 mole) at reflux for 16 hrs., and concentrating in vacuo to an oil. A solution of 2-deoxy-2-fluoro-3,5-di-O-benzoylarabinofuranosyl bromide (6.5 g, 0.0.38 mole, as obtained in Procedure 5) in 90 mL of CH₂Cl₂ is stirred at 25° C., and a solution of 2,4-di-O-trimethylsilyl-5-iodouracil (6.15 g, 0.0161 mole) in 30 ml CH₃CN containing 2.3 g (0.0154 mole) of NaI is added thereto. The resulting slurry is stirred for 5 days at room temperature. The room temperature reaction is monitored by HPLC for the disappearance of the furanosyl bromide. The reaction mixture is diluted with 50 mL CH₂Cl₂, quenched with 20% Na₂S₂O₃ in H₂O, and the mixture stirred with decolorizing carbon for 1 hr., and filtered. The filtrate layers are separated, and the bright yellow CH₂Cl₂ layer dried (Na₂SO₄), and concentrated at reduced pressure to approximately 25 mL. Analysis by HPLC indicates the presence of the product with an α/β ratio of 1/5. HPLC is done on a Whatman C-18 Reverse Phase Column, using 50% CH₃CN/H₂O with UV detection at 282 nm. The 2-deoxy-2-fluoro-3,5-di-O-benzoylarabinofuranosyl bromide elutes at 6.2 min., 1-(2-deoxy-2-fluoro-3,5,di-O-benzoylarabinofuranosyl)-5-iodouracil, α-isomer at 10.26, min., and the β-isomer at 11.44 min. The product crystallizes from CH₂Cl₂, and is further precipitated by the addition of 1.5 volumes of hexane and chilling in an ice bath for 1 hr. The 1-(2-deoxy-2-fluoro-3,5-di-O-benzoyl-β-arabinofuranosyl)-5-iodouracil is collected by filtration and dried; yield 3.3 g 41.2% of theory. This material assayed by HPLC quantitation as 96% pure (mp 197°) [360 MHz NMR (DMSO): 6.35, d, 1H; 5.78, s, 1H; 5.73, dd, 1H; 5.58, dd, 1H; 4.8, m, 2H; 4.68, dd, 1H; 7.5–8.2, m, 16H. Elemental analysis calculated: %C 47.60, %H 3.13, %N 4.83; Found: %C 44.74 %H 3.09, %N 4.42. IR (KBr) aromatic 3060, 1610 cm⁻¹; NH, OH 3180, 3060 cm⁻¹; ester, CO—NH—CO 1720, 1665, 1265 cm⁻¹.]

Procedure 7 (Step 8)
1-(2-Deoxy-2-fluoro-α-D-arabinofuranosyl)-5-iodouracil (Formula IX).

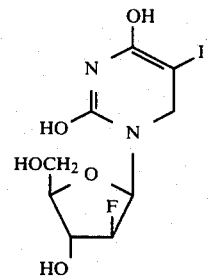

A slurry of 1-(2-deoxy-2-fluoro-3,5-di-O-benzoyl-β-D-arabinofuranosyl)-5-iodouracil (4.7 g, 0.0081 mole) from Procedure 6 in 60 mL 50% MeOH/H₂O is stirred at 25° C. maintained at pH 10.5 with 3N NaOH until complete dissolution of solid occurs. Progress of the hydrolysis is followed by HPLC (mobile phase=70% H₂O/30% MeOH, flow rate=1 mL/min., wave length=282 nm UV detection, column=Whatman 10 ODS-3 reverse-phase 25 cm., injection volume=20 μl at ~0.5 mg/l concentration, α-IX=6.86 min., β-IX=7.98 min., and 5-iodouracil=4.5 min.). When the reaction is complete (16 hr.), 25 mL of water is added and the mixture is concentrated to approximately 30 mL. The clear aqueous concentrate is adjusted to pH 6.5 to 7.0 with 3N HCl. A solid forms, the mixture is stirred at 25° C. for 2 hrs., and at 0° to 5° C. for 5 hrs. The solid is collected by filtration, washed with 30 mL cold H₂O and dried at 50° C./5 mm. The yield of product is 2.7 g (90%), mp 223°–226° [360 MHz NMR (CD₃OD) 8.28, d, 1H; 6.16, dd, 1H; 5.04, m, 1H; 4.32, m, 1H; 3.95–3.7, m, 3H. Elemental analysis calculated: %C 29.05, %H 2.71, %N 7.53; Found: %C 28.86, %H 2.64, %N 7.50; IR (KBr) NH, OH 3400, 3200 cm⁻¹; CO—N-H—CO 1725, 1655 cm⁻¹, C—O 1050 cm⁻¹.]

The following pyrimidine compounds are substituted in Procedure 6 for 5-iodouracil with modification of the amount of hexamethyldisilazane employed as may be required for complete silylation of the pyrimidine reactant prior to reaction thereof with the arabinofuranosyl bromide derivative. The remainder of the transformations are carried out substantially as described to produce first the corresponding 1-(3,5-di-O-benzoyl-2-deoxy-2-fluoro-β-D-arabinofuranosyl)pyrimidine derivative and thereafter the 1-(2-deoxy-2-fluoro-β-D-arabinofuranosyl)pyrimidine derivative.

5-chlorouracil,
5-bromouracil,
5-fluorouracil,
6-azathymine,
5-bromocytosine,
5-chlorocytosine,
5-fluorocytosine,
5-iodocytosine,
5-methylcytosine,
5-ethylcytosine,
5-benzoylcytosine,
5-phenylcytosine,
5-vinylcytosine,
5-ethynylcytosine,
5-aminocytosine,
5-benzylaminocytosine, 5-aminomethylcytosine,
5-hydroxymethylcytosine,
5-methyl-6-azacytosine,
thymine,
6-azathymine,
5-napthylcytosine,
5-methylaminocytosine,
5-dimethylaminocytosine,

We claim:

1. The 2-deoxy-2-fluoroarabinoside having Formula VIa

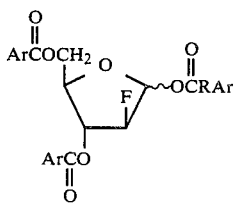

wherein Ar is phenyl, naphthyl, substituted phenyl, or substituted naphthyl and said substituent contains up to 4 carbon atoms and is selected from alkyl, alkoxyl, halo, nitro, and dinitro and the 1-α configuration.

2. The compound of claim 1 wherein Ar is selected from the group consisting of phenyl, tolyl, bromophenyl, chlorophenyl, nitrophenyl, and dinitrophenyl.

3. The compound of claim 1, 2-deoxy-2-fluoro-1,3,5-tri-O-benzoylarabinofuranoside.

4. The process of claim 3 wherein said liquid organic reaction medium is said compound of the formula $R^aOAlkOR^b$.

5. The compound of claim 4 wherein Ar is selected from the group consisting of phenyl, tolyl, bromophenyl, chlorophenyl, nitrophenyl, and dinitrophenyl.

6. The compound of claim 4, 1,3,5-tri-O-benzoyl-2-O-(1-imidazosulfonyl)ribofuranoside.

7. The compound of claim 4, 1,3,5-tri-O-benzoyl-2-O-fluorosulfonylribofuranoside.

* * * * *